(12) United States Patent
Inukai et al.

(10) Patent No.: US 6,506,923 B2
(45) Date of Patent: Jan. 14, 2003

(54) PREPARATION OF ORGANOHALOSILANES

(75) Inventors: Tetsuya Inukai, Annaka (JP); Susumu Ueno, Annaka (JP); Toshio Shinohara, Annaka (JP); Mikio Aramata, Annaka (JP); Yoichi Tanifuji, Tokyo (JP); Hajime Ishizaka, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/074,025

(22) Filed: Feb. 14, 2002

(65) Prior Publication Data

US 2002/0156310 A1 Oct. 24, 2002

(30) Foreign Application Priority Data

Feb. 14, 2001 (JP) .......................... 2001-037174

(51) Int. Cl.$^7$ .................................. C07F 7/16
(52) U.S. Cl. ........................ 556/472; 536/466
(58) Field of Search ................. 556/472, 466

(56) References Cited

U.S. PATENT DOCUMENTS

| | | | |
|---|---|---|---|
| 2,380,995 A | | 8/1945 | Rochow |
| 4,500,724 A | | 2/1985 | Ward, III et al. |
| 4,602,101 A | | 7/1986 | Halm et al. |
| 4,895,969 A | * | 1/1990 | Feldner et al. ............... 556/472 |
| 5,015,751 A | * | 5/1991 | Feldner et al. ............... 556/472 |
| 5,059,706 A | | 10/1991 | Degen et al. |
| 6,005,130 A | | 12/1999 | Lewis et al. |
| 6,025,513 A | | 2/2000 | Nakanishi et al. |

FOREIGN PATENT DOCUMENTS

| | | |
|---|---|---|
| JP | 5-51596 | 8/1993 |
| JP | 6-92421 | 11/1994 |
| JP | 2000-254506 | 9/2000 |
| JP | 2000-296334 | 10/2000 |
| SU | 122749 | 1/1959 |
| SU | 178817 | 3/1966 |
| SU | 237892 | 11/1969 |

OTHER PUBLICATIONS

F. Komitsky et al., Silicon for the Chemical Industry IV, Geiranger, Norway (1998), p. 217.

L. Rosch, W. Kalchaucer et al., Silicon for the Chemical Industry IV, Sandefjord, Norway (1996).

* cited by examiner

Primary Examiner—Paul F. Shaver
(74) Attorney, Agent, or Firm—Birch, Stewart, Kolasch & Birch, LLP

(57) ABSTRACT

In a process for preparing oganohalosilanes by reacting metallic silicon particles with an organohalide in the presence of a copper catalyst, a contact mass composed of the metallic silicon and the catalyst further contains a minute, but effective amount of a catalytic metal powder which has been produced by an atomizing technique. The process is successful in drastically increasing a formation rate without lowering the selectivity of useful silane.

5 Claims, No Drawings

PREPARATION OF ORGANOHALOSILANES

This invention relates to an industrial process for preparing organohalosilanes.

BACKGROUND OF THE INVENTION

With respect to the synthesis of alkylhalosilanes, Rochow first disclosed in U.S. Pat. No. 2,380,995 direct synthesis reaction between metallic silicon and alkyl halide in the presence of a copper catalyst. Since then, there have been reported a number of research works relating to various co-catalysts used together with copper catalysts, reactors, additives used during reaction, and the like. In the industrial synthesis of organohalosilanes, the selectivity of diorganodihalosilane which is most widely used in silicone resins, the formation rate of silanes, and the percent conversion of metallic silicon into useful silane are crucial. The selectivity of diorganodihalosilane is evaluated in terms of a weight or molar ratio of dialkyldihalosilane to the silanes produced and a T/D ratio. Organohalosilane products contain diorganodihalosilane (D), triorganohalosilane (M), organotrihalosilane (T), etc. as well as other by-products such as organohydrodihalosilane (H) and organohalodisilane. In particular, disilanes are known as a high-boiling fraction among silicone manufacturers because few processes are available for the effective utilization of disilanes, and most disilanes are discarded. The T/D ratio is a compositional ratio of organotrihalosilane to diorganodihalosilane in the entire organohalosilanes produced, with a lower T/D ratio being preferred. The formation rate of organohalosilane is represented by a space time yield (STY) which is the weight of crude organohalosilane produced per unit time relative to the weight of metallic silicon held in the reactor. In order to improve the content of diorganohalosilane produced, reduce the T/D ratio or increase the STY, various research works have been made with a focus on the catalyst and co-catalyst.

USSR Application Specification No. 617,569 (Certificate of inventorship No. 122,749) dated Jan. 24, 1959 discloses reaction in the presence of metallic silicon-copper alloy with 20 to 40 ppm of antimony added. Allegedly, the dimethyldichlorosilane content is improved from 40% to 60%. U.S. Pat. No. 4,500,724 discloses use of a copper/zinc/tin catalyst containing 200 to 3,000 ppm of tin, thereby achieving an improvement of T/D to 0.037. Japanese Patent Publication (JP-B) No. 6-92421 discloses reaction using copper arsenide having an arsenic concentration of at least 50 ppm. It is described in these patent references that reactivity, more specifically the rate of reaction of metallic silicon is improved by adding these tin, antimony and arsenic co-catalysts to a reaction contact mass comprising metallic silicon and copper.

USSR Application Specification No. 903,369 (Certificate of inventorship No. 178,817) dated Jun. 2, 1964 discloses that a co-catalyst selected from the group consisting of zinc, bismuth, phosphorus (200 ppm), arsenic, tin, and iron improves the dimethyldichlorosilane content to 72.1% from the value achieved by the above-referred Application Specification No. 617,569 (Certificate of inventorship No. 122, 749). Also USSR Application Specification No. 1,152,943 (Certificate of inventorship No. 237,892) dated Nov. 20, 1969 discloses to add a phosphorus-copper-silicon alloy to a contact mass so as to give 2,500 to 30,000 ppm of phosphorus, thereby improving the dimethyldichlorosilane content to 82.3%. Moreover, U.S. Pat. No. 4,602,101 corresponding to JP-B 5-51596 discloses that 25 to 2,500 ppm of a phosphorus compound capable of generating elemental phosphorus in the reactor is added to a contact mass. Although the results of reaction according to this U.S. patent are improved over the last-mentioned USSR patent, there still remain many problems including hazard imposed by spontaneously igniting elemental phosphorus and increased cost of raw materials. Then this US patent is also unsuitable to apply to commercial scale reactors. Also, F. Komitsky et al., Silicon For the Chemical Industry IV, Geiranger, Norway (1998), page 217, proposes the addition of phosphorus in the form of copper phosphide, leaving problems including a low percent conversion, ineffective utilization of phosphorus, and difficult control of a phosphorus concentration. U.S. Pat. No. 6,025,513 discloses to add boron to a contact mass wherein the boron concentration is controlled so as to improve productivity. U.S. Pat. No. 5,059,706 discloses to introduce a phosphorus compound in a vapor phase into a reactor for increasing selectivity. U.S. Pat. No. 6,005,130 discloses to introduce organomonophosphine for increasing selectivity.

However, the phosphorus base additives used in the prior art have an outstanding trade-off between activity and composition selectivity. In particular, it is pointed out that oxide originating from phosphorus can exacerbate flow on the particle surface. Therefore, the conventional phosphorus base additives offer few merits on the continuous operation of commercial scale reactors. Other additives are known from L. Rosch, W. Kalchauer et al., Silicon for the Chemical Industry IV, Sandefjord, Norway (1996) wherein monomethyldichlorosilane is introduced for improving activity. This additive is effective only at the initial period, but not regarded as exerting a lasting effect during the continuous operation of commercial scale reactors.

As seen from the above discussion, engineers involved in most of the above-referred proposals were interested in elements of which the catalyst is made. A more recent approach for improving catalysis was made from a new standpoint. For example, JP-A 2000-254506 discloses an industrial organohalosilane production process using a thermally active metallic copper powder having substantial strain energy. JP-A 2000-296334 discloses an industrial organohalosilane production process using a copper powder in the form of flakes or scales.

However, the organohalosilane synthesis reaction in these processes is heterogeneous gas-solid reaction in a fluidized bed, agitated fluidized bed or fixed bed. The results of reaction largely depend on the powder behavior of the contact mass or catalyst. In particular, since the copper catalyst and co-catalyst are used in excess in the industry, the powder in the contact mass can agglomerate, interfering with the flow of the contact mass and detracting from productivity.

SUMMARY OF THE INVENTION

An object of the invention is to provide a novel and improved process for preparing organohalosilanes at a drastically increased formation rate without lowering the selectivity of useful silane.

Intending to solve the actual drawback encountered in the practice of the prior art direct method or Rochow method, that is, the drawback that the copper catalyst and co-catalyst used in excess causes the powder in the contact mass to agglomerate to interfere with the flow of the contact mass and detract from productivity, we have made efforts to establish a catalyst system capable of satisfying both the chemical action of the catalyst and the flow of the catalyst powder and the contact mass containing the same. We have discovered that the preparation of organohalosilanes is improved by adding to the contact mass an effective amount of a catalytic metal powder which has been produced by an atomizing technique.

More specifically, we have found that the formation rate of useful silane is drastically increased by adding an atomized catalytic metal powder to the contact mass rather than a resinous powder by an electrolytic method, an angular or flaky powder by stamping and grinding methods, a powder by heat treatment, and a flaky or microcrystalline powder from a chemically reduced powder.

We learned that in designing the function of a catalyst in the direct method, the powder performance of a catalyst powder and a contact mass containing the same is largely dependent on how to prepare the catalyst powder. It has been found that an atomized catalyst powder contains more spherical particles and is advantageously applicable to the direct method. The invention uses an atomized catalytic metal powder in the direct method to form a contact mass which contains a minute, but effective amount of spherical particles so that the flow of powder in the contact mass is facilitated, thereby improving the formation rate of useful silane and preserving such an improved rate. This concept completely differs from the modified formulations in the prior art relying on the action of short life catalysts. Based on this concept, we made a study on a series of catalytic metal powders which are produced by various atomizing techniques. We have found that when organohalosilanes are synthesized by reacting metallic silicon with organohalide in the presence of a copper catalyst, introducing in the contact mass a minute, but effective amount of an atomized catalytic metal powder is effective for increasing the formation rate, yet does not reduce the proportion of useful silane in the product, thus succeeding in producing organohalosilanes in high yields.

Accordingly, the invention provides a process for preparing oganohalosilanes, comprising the step of reacting metallic silicon particles with an organohalide in the presence of a copper catalyst, wherein a contact mass composed of the metallic silicon and the catalyst further contains as a catalyst component an effective amount of a catalytic metal powder which has been produced by an atomizing technique.

DESCRIPTION OF THE PREFERRED EMBODIMENT

The process for preparing oganohalosilanes according to the invention involves the step of reacting metallic silicon particles with an organohalide RX in the presence of a copper catalyst to form organohalosilanes of the following general formula (1):

$$R_nH_mSiX_{4-n-m} \quad (1)$$

wherein R is a monovalent hydrocarbon group, X is a halogen atom, n and m each are an integer of 0 to 3, and the sum of n and m is 1 to 3.

The metallic silicon used herein preferably has a silicon purity of at least 97% by weight, especially at least 98% by weight. Prior to use, the metallic silicon is preferably ground into particles with an appropriate particle size. Where the reactor used is a fluidized bed or stirred bed reactor, the metallic silicon powder should preferably have a particle size in the range of 5 to 150 µm, corresponding to 50% of the mass base cumulative size distribution curve on sieving, in order that the metallic silicon powder have good fluidity.

The organohalide is represented by RX wherein R is a monovalent hydrocarbon group and X is a halogen atom.

The monovalent hydrocarbon groups represented by R are generally those of 1 to 10 carbon atoms, especially 1 to 6 carbon atoms, for example, alkyl, aryl and aralkyl groups, and more preferably methyl and phenyl, with methyl being most preferred. The halogen atoms represented by X are usually Cl and Br. Illustrative examples of the organohalide include methyl chloride, ethyl chloride, propyl chloride, methyl bromide, ethyl bromide, benzene chloride and benzene bromide. Of these, methyl chloride and benzene chloride are preferable. Methyl chloride is most useful in the industry because dimethyldichlorosilane produced therefrom finds a wide variety of applications as the raw material for many silicone resins.

In formula (1), n and m each are an integer of 0 to 3, and n+m is 1 to 3. The predominant component is the compound wherein n=2 (R is a monovalent hydrocarbon group) and m=0. It is preferred that the organohalosilane product contain at least 80%, more preferably at least 85% by weight of the compound wherein n=2 and m=0.

The copper catalyst used herein may be selected from various forms of copper including elemental copper (or metallic copper) such as powdered copper and stamped copper, and copper compounds such as cuprous oxide, cupric oxide, copper halides (e.g., copper chloride) and copper acetate. Any of promoters such as zinc, tin, antimony and arsenic may be used as the co-catalyst. The co-catalyst may be used alone or in the form of an alloy with copper. Exemplary copper alloys are Cu—Zn, Cu—Sn, and Cu—Zn—Sn (or Sb or As). Examples of the co-catalyst which is used alone include zinc compounds such as metallic zinc, zinc chloride, zinc oxide, and zinc acetate, tin compounds such as metallic tin, tin chloride and tin oxide, antimony compounds such as metallic antimony, antimony chloride and antimony oxide, aluminum compounds such as metallic aluminum, aluminum chloride and aluminum oxide, metallic phosphorus, inorganic phosphorus compounds such as phosphorus trichloride and phosphorus oxide, and alkylphosphines such as trimethylphosphine and triphenylphosphine. The copper catalyst and co-catalyst may be separately admitted into the reactor.

An appropriate amount of the copper catalyst blended is about 0.1 to 10 parts, and more preferably about 2 to 8 parts by weight per 100 parts by weight of the metallic silicon powder. The amount of the co-catalyst blended is suitably determined among the commonly used amounts depending on its type and form. For example, zinc is used in an amount of 0.05 to 1 part by weight per 100 parts by weight of the metallic silicon powder. Tin, antimony and arsenic are used in a single or total amount of 0.001 to 0.05 part, especially 0.005 to 0.01 part by weight per 100 parts by weight of the metallic silicon powder.

According to the invention, a catalytic metal powder which has been produced by an atomizing technique is used in addition to the copper catalyst in order to increase the formation rate of useful silane. The invention is based on the discovery that using a contact mass containing a minute, but effective amount of a catalytic metal powder which has been produced by an atomizing technique, the formation rate of silanes is drastically increased without substantially altering the composition of useful silane.

The atomized catalytic metal powder is preferably a copper powder, a brass powder, a bronze powder or a catalytic alloy powder containing two or more elements selected from among copper, zinc, tin, phosphorus, nickel, cobalt, iron, manganese, chromium, tungsten, molybdenum, boron, silicon and carbon. Preferred are copper and copper alloys containing at least 50%, especially at least 70% by weight of copper. The atomizing technique by which the metal powder is produced is selected from among a gas atomizing technique, vacuum atomizing technique, water atomizing technique, centrifugal atomizing technique, rotating electrode technique, and rotating coolant fluid technique. The atomized catalytic metal powder preferably has a specific surface area of 0.01 to 0.5 m$^2$/g, especially 0.05 to 0.3 m$^2$/g, as measured by either the BET adsorption method or the air-permeability method.

In order to improve the productivity of organohalosilanes, the atomized catalytic metal powder is used in an effective amount, depending on the reaction time, scale, and the quality of metallic silicon. The effective amount of the atomized catalytic metal powder is preferably 0.01 to 5%, especially 0.05 to 3% by weight based on the entire weight of silicon.

The process of the invention can be carried out in any of fixed bed reactors, stirred bed reactors and fluidized bed reactors. From the industrial aspect, a fluidized bed reactor suited for continuous operation is employed. Reaction is effected at a temperature of about 250 to 600° C.

In the step of heating the contact mass or imparting catalytic activity to the contact mass, an inert gas is used for fluidizing the contact mass in the reactor. Such an inert gas may be nitrogen, helium or argon gas, for example, with the nitrogen gas being preferable from the economic standpoint. The flow velocity of the inert gas fed in this and subsequent steps is at least the incipient fluidization velocity of the contact mass, and preferably about 5 times the incipient fluidization velocity. A flow velocity below the range of the inert gas may often fail to achieve uniform fluidization of the contact mass. If the flow velocity of the inert gas is above the range, metallic silicon powder may be excessively scattered with increased losses of the inert gas and heat. It is recommended to recycle the inert gas and the organohalide.

After the contact mass is given catalytic activity as mentioned above, the organohalide is introduced into the reactor where gas-solid catalytic reaction takes place between the organohalide and metallic silicon to form organohalosilanes. The organohalide is previously heated and gasified before it is admitted into the reactor. The organohalide gas may be fed alone or combined with an inert gas in a sufficient amount to fluidize the contact mass, the fluidizing amount being determined as appropriate from the diameter of the reactor and the superficial velocity.

EXAMPLE

Examples of the invention are given below by way of illustration and not by way of limitation. Parts are by weight.

Comparative Example 1

A fluidized bed reactor of carbon steel having a diameter of 75 mm and a height of 900 mm was charged with 100 parts of metallic silicon powder and 4 parts of a catalyst in the form of metallic copper powder. Then a gas mixture of methyl chloride and nitrogen was introduced into the reactor at a rate of 14.4 Nl/min and the reactor was heated at a temperature of 310° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 7 times. Reported in Table 1 are the concentrations of impurities in the metallic silicon used, an average of silane formation rate from the start to the end of reaction, and an average quantity of useful silane (i.e., yield of dimethyldichlorosilane).

Comparative Example 2

A fluidized bed reactor of carbon steel having a diameter of 75 mm and a height of 900 mm was charged with 100 parts of metallic silicon powder and 5 parts of a catalyst in the form of copper oxide powder. Then a gas mixture of methyl chloride and nitrogen was introduced into the reactor at a rate of 14.4 Nl/min and the reactor was heated at a temperature of 320° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Reported in Table 1 are the concentrations of impurities in the metallic silicon used, an average of silane formation rate from the start to the end of reaction, and an average quantity of useful silane.

Example 1

A fluidized bed reactor of carbon steel having a diameter of 75 mm and a height of 900 mm was charged with 100 parts of metallic silicon powder, 4 parts of a catalyst in the form of metallic copper powder and 0.5 part of an atomized metal powder composed of 100% Cu and having a BET surface area of 0.10 m$^2$/g. Then a gas mixture of methyl chloride and nitrogen was introduced into the reactor at a rate of 14.4 Nl/min and the reactor was heated at a temperature of 310° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average of silane formation rate from the start to the end of reaction, and an average quantity of useful silane.

Example 2

A fluidized bed reactor of carbon steel having a diameter of 75 mm and a height of 900 mm was charged with 100 parts of metallic silicon powder, 5 parts of a catalyst in the form of copper oxide powder and 0.4 part of an atomized metal powder composed of 100% Cu and having a BET surface area of 0.10 m$^2$/g. Then a gas mixture of methyl chloride and nitrogen was introduced into the reactor at a rate of 14.4 Nl/min and the reactor was heated at a temperature of 320° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 3

A fluidized bed reactor of carbon steel having a diameter of 75 mm and a height of 900 mm was charged with 100 parts of metallic silicon powder, 4 parts of a catalyst in the form of metallic copper powder and 0.5 part of an atomized copper alloy powder composed of 90% Cu and 10% Zn and having a BET surface area of 0.12 m$^2$/g. Then a gas mixture of methyl chloride and nitrogen was introduced into the reactor at a rate of 14.4 Nl/min and the reactor was heated at a temperature of 310° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 4

A fluidized bed reactor of carbon steel having a diameter of 75 mm and a height of 900 mm was charged with 100 parts of metallic silicon powder, 5 parts of a catalyst in the form of copper oxide powder and 0.4 part of an atomized copper alloy powder composed of 90% Cu and 10% Zn and having a BET surface area of 0.12 $m^2/g$. Then a gas mixture of methyl chloride and nitrogen was introduced into the reactor at a rate of 14.4 Nl/min and the reactor was heated at a temperature of 320° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 5

A fluidized bed reactor of carbon steel having a diameter of 75 mm and a height of 900 mm was charged with 100 parts of metallic silicon powder, 4 parts of a catalyst in the form of metallic copper powder and 0.5 part of an atomized copper alloy powder composed of 95% Cu and 5% Sn and having a BET surface area of 0.11 $m^2/g$. Then a gas mixture of methyl chloride and nitrogen was introduced into the reactor at a rate of 14.4 Nl/min and the reactor was heated at a temperature of 310° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 6

A fluidized bed reactor of carbon steel having a diameter of 75 mm and a height of 900 mm was charged with 100 parts of metallic silicon powder, 5 parts of a catalyst in the form of copper oxide powder and 0.1 part of an atomized copper alloy powder composed of 95% Cu and 5% Sn and having a BET surface area of 0.11 $m^2/g$. Then a gas mixture of methyl chloride and nitrogen was introduced into the reactor at a rate of 14.4 Nl/min and the reactor was heated at a temperature of 320° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 7

A fluidized bed reactor of carbon steel having a diameter of 75 mm and a height of 900 mm was charged with 100 parts of metallic silicon powder, 4 parts of a catalyst in the form of metallic copper powder and 0.5 part of an atomized copper alloy powder composed of 64% Cu, 18% Ni and 18% Zn and having a BET surface area of 0.14 $m^2/g$. Then a gas mixture of methyl chloride and nitrogen was introduced into the reactor at a rate of 14.4 Nl/min and the reactor was heated at a temperature of 310° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 8

A fluidized bed reactor of carbon steel having a diameter of 75 mm and a height of 900 mm was charged with 100 parts of metallic silicon powder, 5 parts of a catalyst in the form of copper oxide powder and 0.4 part of an atomized copper alloy powder composed of 64% Cu, 18% Ni and 18% Zn and having a BET surface area of 0.14 $m^2/g$. Then a gas mixture of methyl chloride and nitrogen was introduced into the reactor at a rate of 14.4 Nl/min and the reactor was heated at a temperature of 320° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 9

A fluidized bed reactor of carbon steel having a diameter of 75 mm and a height of 900 mm was charged with 100 parts of metallic silicon powder, 4 parts of a catalyst in the form of metallic copper powder and 0.5 part of an atomized copper alloy powder composed of 97% Cu and 3% Co and having a BET surface area of 0.12 $m^2/g$. Then a gas mixture of methyl chloride and nitrogen was introduced into the reactor at a rate of 14.4 Nl/min and the reactor was heated at a temperature of 310° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 10

A fluidized bed reactor of carbon steel having a diameter of 75 mm and a height of 900 mm was charged with 100 parts of metallic silicon powder, 5 parts of a catalyst in the form of copper oxide powder and 0.4 part of an atomized copper alloy powder composed of 97% Cu and 3% Co and having a BET surface area of 0.12 $m^2/g$. Then a gas mixture of methyl chloride and nitrogen was introduced into the reactor at a rate of 14.4 Nl/min and the reactor was heated at a temperature of 320° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 11

A fluidized bed reactor of carbon steel having a diameter of 75 mm and a height of 900 mm was charged with 100 parts of metallic silicon powder, 4 parts of a catalyst in the form of metallic copper powder and 0.5 part of an atomized copper alloy powder composed of 91% Cu, 4% Fe and 5% Mn and having a BET surface area of 0.10 m$^2$/g. Then a gas mixture of methyl chloride and nitrogen was introduced into the reactor at a rate of 14.4 Nl/min and the reactor was heated at a temperature of 310° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 12

A fluidized bed reactor of carbon steel having a diameter of 75 mm and a height of 900 mm was charged with 100 parts of metallic silicon powder, 5 parts of a catalyst in the form of copper oxide powder and 0.4 part of an atomized copper alloy powder composed of 91% Cu, 4% Fe and 5% Mn and having a BET surface area of 0.10 m$^2$/g. Then a gas mixture of methyl chloride and nitrogen was introduced into the reactor at a rate of 14.4 Nl/min and the reactor was heated at a temperature of 320° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 13

A fluidized bed reactor of carbon steel having a diameter of 75 mm and a height of 900 mm was charged with 100 parts of metallic silicon powder, 4 parts of a catalyst in the form of metallic copper powder and 0.02 part of an atomized metal powder composed of 100% Sn and having a BET surface area of 0.15 m$^2$/g. Then a gas mixture of methyl chloride and nitrogen was introduced into the reactor at a rate of 14.4 Nl/min and the reactor was heated at a temperature of 310° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 14

A fluidized bed reactor of carbon steel having a diameter of 75 mm and a height of 900 mm was charged with 100 parts of metallic silicon powder, 5 parts of a catalyst in the form of copper oxide powder and 0.02 part of an atomized metal powder composed of 100% Sn and having a BET surface area of 0.15 m$^2$/g. Then a gas mixture of methyl chloride and nitrogen was introduced into the reactor at a rate of 14.4 Nl/min and the reactor was heated at a temperature of 320° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 15

A fluidized bed reactor of carbon steel having a diameter of 75 mm and a height of 900 mm was charged with 100 parts of metallic silicon powder, 4 parts of a catalyst in the form of metallic copper powder and 0.3 part of an atomized copper alloy powder composed of 85% Cu and 15% P and having a BET surface area of 0.09 m$^2$/g. Then a gas mixture of methyl chloride and nitrogen was introduced into the reactor at a rate of 14.4 Nl/min and the reactor was heated at a temperature of 310° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 16

A fluidized bed reactor of carbon steel having a diameter of 75 mm and a height of 900 mm was charged with 100 parts of metallic silicon powder, 5 parts of a catalyst in the form of copper oxide powder and 0.3 part of an atomized copper alloy powder composed of 85% Cu and 15% P and having a BET surface area of 0.09 m$^2$/g. Then a gas mixture of methyl chloride and nitrogen was introduced into the reactor at a rate of 14.4 Nl/min and the reactor was heated at a temperature of 320° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 17

A fluidized bed reactor of carbon steel having a diameter of 75 mm and a height of 900 mm was charged with 100 parts of metallic silicon powder, 4 parts of a catalyst in the form of metallic copper powder and 0.3 part of an atomized copper alloy powder composed of 92% Cu and 8% P and having a BET surface area of 0.07 m$^2$/g. Then a gas mixture of methyl chloride and nitrogen was introduced into the reactor at a rate of 14.4 Nl/min and the reactor was heated at a temperature of 310° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 18

A fluidized bed reactor of carbon steel having a diameter of 75 mm and a height of 900 mm was charged with 100 parts of metallic silicon powder, 5 parts of a catalyst in the form of copper oxide powder and 0.3 part of an atomized copper alloy powder composed of 92% Cu and 8% P and having a BET surface area of 0.07 m²/g. Then a gas mixture of methyl chloride and nitrogen was introduced into the reactor at a rate of 14.4 Nl/min and the reactor was heated at a temperature of 320° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 19

A fluidized bed reactor of carbon steel having a diameter of 75 mm and a height of 900 mm was charged with 100 parts of metallic silicon powder, 4 parts of a catalyst in the form of metallic copper powder and 0.3 part of an atomized alloy powder composed of 90% Ni and 10% P and having a BET surface area of 0.13 m²/g. Then a gas mixture of methyl chloride and nitrogen was introduced into the reactor at a rate of 14.4 Nl/min and the reactor was heated at a temperature of 310° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

Example 20

A fluidized bed reactor of carbon steel having a diameter of 75 mm and a height of 900 mm was charged with 100 parts of metallic silicon powder, 5 parts of a catalyst in the form of copper oxide powder and 0.3 part of an atomized alloy powder composed of 90% Ni and 10% P and having a BET surface area of 0.13 m²/g. Then a gas mixture of methyl chloride and nitrogen was introduced into the reactor at a rate of 14.4 Nl/min and the reactor was heated at a temperature of 320° C. whereupon reaction continued. Metallic silicon powder and the catalyst were fed from the reactor bottom so as to keep constant the amount of the contact mass in the reactor. Reaction was continued for 10 hours, following which the reaction was terminated. The run was repeated 2 times. Table 1 reports the concentrations of impurities in the metallic silicon used, an average silane formation rate, and an average quantity of useful silane.

TABLE 1

| | Reaction temp. (° C.) | Impurities Fe (%) | Al (%) | Ca (%) | Atomized metal powder Type | concentration[a] (%/Si) | BET surface area (m²/g) | Formation rate[b] (g/h) | Useful silane quantity[c] (%) |
|---|---|---|---|---|---|---|---|---|---|
| CE1 | 310 | 0.26 | 0.13 | 0.07 | — | — | — | 276 | 87.7 |
| CE2 | 320 | 0.28 | 0.14 | 0.06 | — | — | — | 259 | 85.9 |
| E1  | 310 | 0.28 | 0.12 | 0.06 | Cu powder[1] | 0.5 | 0.10 | 418 | 89.4 |
| E2  | 320 | 0.28 | 0.17 | 0.06 | Cu powder[1] | 0.4 | 0.10 | 408 | 88.1 |
| E3  | 310 | 0.28 | 0.12 | 0.06 | Cu alloy powder[2] | 0.5 | 0.12 | 406 | 89.8 |
| E4  | 320 | 0.27 | 0.17 | 0.07 | Cu alloy powder[2] | 0.4 | 0.12 | 384 | 87.3 |
| E5  | 310 | 0.28 | 0.12 | 0.06 | Cu alloy powder[3] | 0.1 | 0.11 | 528 | 90.4 |
| E+  | 320 | 0.27 | 0.17 | 0.07 | Cu alloy powder[3] | 0.1 | 0.11 | 506 | 89.6 |
| E7  | 310 | 0.27 | 0.11 | 0.09 | Cu alloy powder[4] | 0.5 | 0.14 | 418 | 88.0 |
| E8  | 320 | 0.27 | 0.14 | 0.07 | Cu alloy powder[4] | 0.5 | 0.14 | 408 | 87.5 |
| E9  | 310 | 0.27 | 0.11 | 0.09 | Cu alloy powder[5] | 0.5 | 0.12 | 466 | 89.4 |
| E10 | 320 | 0.27 | 0.14 | 0.07 | Cu alloy powder[5] | 0.4 | 0.12 | 449 | 88.0 |
| E11 | 310 | 0.28 | 0.12 | 0.06 | Cu alloy powder[6] | 0.5 | 0.10 | 482 | 89.2 |
| E12 | 320 | 0.25 | 0.18 | 0.06 | Cu alloy powder[6] | 0.4 | 0.10 | 454 | 87.1 |
| E13 | 310 | 0.28 | 0.12 | 0.06 | Metal powder[7] | 0.02 | 0.15 | 504 | 87.4 |
| E14 | 320 | 0.25 | 0.18 | 0.07 | Metal powder[7] | 0.02 | 0.15 | 482 | 90.3 |
| E15 | 310 | 0.28 | 0.12 | 0.06 | Cu alloy powder[8] | 0.3 | 0.09 | 449 | 90.2 |
| E16 | 320 | 0.28 | 0.12 | 0.06 | Cu alloy powder[8] | 0.3 | 0.09 | 427 | 89.9 |
| E17 | 310 | 0.26 | 0.18 | 0.07 | Cu alloy powder[9] | 0.3 | 0.07 | 470 | 90.3 |
| E18 | 310 | 0.26 | 0.18 | 0.07 | Cu alloy powder[9] | 0.3 | 0.07 | 456 | 89.2 |
| E19 | 310 | 0.28 | 0.12 | 0.06 | Alloy powder[10] | 0.3 | 0.13 | 451 | 89.3 |
| E20 | 320 | 0.27 | 0.14 | 0.07 | Alloy powder[10] | 0.3 | 0.13 | 427 | 87.9 |

Note:
[a] the concentration (wt %) of atomized metal powder based on the weight of silicon
[b],[c] an average of 7 runs for Comparative Example 1 and an average of 2 runs for Comparative Example 2 and Examples 1 to 20
[1] atomized metal powder composed of 100% Cu
[2] atomized alloy powder composed of 90% Cu and 10% Zn
[3] atomized alloy powder composed of 95% Cu and 5% Sn
[4] atomized alloy powder composed of 64% Cu, 18% Ni and 18% Zn
[5] atomized alloy powder composed of 97% Cu and 3% Co
[6] atomized alloy powder composed of 91% Cu, 4% Fe and 5% Mn
[7] atomized metal powder composed of 100% Sn
[8] atomized alloy powder composed of 85% Cu and 15% P
[9] atomized alloy powder composed of 92% Cu and 8% P
[10] atomized alloy powder composed of 90% Ni and 10% P There has been described a process for preparing organohalosilanes using a contact mass containing a minute, but effective amount of an atomized catalytic metal powder, thereby drastically increasing the formation rate without lowering the selectivity of useful silane.

Japanese Patent Application No. 2001-037174 is incorporated herein by reference.

Reasonable modifications and variations are possible from the foregoing disclosure without departing from either the spirit or scope of the present invention as defined by the claims.

What is claimed is:

1. A process for preparing organohalosilanes of the following general formula (1):

$$R_nH_mSiX_{4-n-m} \tag{1}$$

wherein R is a monovalent hydrocarbon group, X is a halogen atom, n and m each are an integer of 0 to 3, and the sum of n and m is 1 to 3, said process comprising the step of reacting an organohalide with metallic silicon particles in the presence of a copper catalyst and in the presence of an effective amount of a metal selected from the group consisting of copper, brass, bronze, and alloys containing two or more members selected from the group consisting of copper, zinc, tin, phosphorus, nickel, cobalt, iron, manganese, chromium, tungsten, molybdenum, boron, and carbon, wherein said metal is in the form of a catalytic metal powder which has been produced by an atomizing technique.

2. The process of claim 1 wherein the contact mass contains an effective amount of a catalytic copper powder or of a catalytic copper alloy powder containing at least 50% by weight of copper, which powder has been produced by an atomizing technique.

3. The process of claim 1 wherein the atomizing technique is selected from the group consisting of a gas atomizing, vacuum atomizing, water atomizing, centrifugal atomizing, rotating electrode, and rotating coolant fluid technique.

4. The process of claim 1 wherein the catalytic metal powder has a specific surface area of 0.01 to 0.5 $m^2/g$ as measured by either the BET adsorption method or the air-permeability method.

5. The process of claim 1 wherein the catalytic metal is at least one member selected from the group consisting of metallic copper, copper compounds, metallic zinc, zinc compounds, metallic tin, tin compounds, metallic antimony, antimony compounds, metallic aluminum, aluminum compounds, metallic phosphorus and phosphorus compounds.

* * * * *